United States Patent [19]

Monte et al.

[11] 4,152,311

[45] May 1, 1979

[54] TITANATE PHOSPHITE ADDUCTS AND THEIR USE

[75] Inventors: Salvatore J. Monte, Staten Island, N.Y.; Gerald Sugerman, Allendale, N.J.

[73] Assignee: Kenrich Petrochemicals, Inc., Bayonne, N.J.

[21] Appl. No.: 847,151

[22] Filed: Oct. 31, 1977

Related U.S. Application Data

[62] Division of Ser. No. 653,772, Jan. 30, 1976, Pat. No. 4,080,353.

[51] Int. Cl.$^2$ .................. C08K 5/18; C08K 5/42; C08K 5/51
[52] U.S. Cl. .................. 260/29.2 EP; 252/431 P; 252/431 N; 260/29.2 E; 260/29.2 K; 260/29.3; 528/485; 528/487
[58] Field of Search ............. 260/29.2 TN, 29.2 EP, 260/2 N, 77.5 AC, 29.3, 29.2 R, 29.2 E; 252/431 P, 431 N

[56] References Cited

U.S. PATENT DOCUMENTS

| | | | |
|---|---|---|---|
| 2,930,785 | 3/1960 | Edmonds | 252/431 P |
| 2,967,856 | 1/1961 | Cooner et al. | 252/431 P |
| 3,244,646 | 4/1966 | Nard et al. | 252/431 P |
| 3,450,797 | 6/1969 | Schäfer et al. | 526/27 X |
| 3,631,142 | 12/1971 | Childers | 526/27 X |
| 3,686,350 | 8/1972 | Ond et al. | 252/431 P |
| 3,766,101 | 10/1973 | Komai et al. | 252/431 P |
| 3,770,839 | 11/1973 | Matsushima | 252/431 P |
| 4,010,145 | 3/1977 | Russin et al. | 252/431 N |

OTHER PUBLICATIONS

Monte et al., "Titanate Coupling Agents–Update 1977" 32nd Annual Conference, SPI Plastics Composites Inst. (Feb., 1977), pp. 1–7, Section 4-E.

*Primary Examiner*—Sandra M. Person
*Attorney, Agent, or Firm*—Bert J. Lewen

[57] ABSTRACT

This invention relates to adducts of tetra-substituted titanates and di-substituted hydrogen phosphites; the use of such adducts for treating particulate fillers, including pigments; the compositions of fillers and the aforesaid adducts with epoxy resins and other casting resins; the reaction product of said adducts with aromatic polyamines; the use of said reaction products for curing epoxide and urethane resins; and compositions of certain of the adducts and casting resins. The titanate-phosphite adducts serve to reduce the viscosity of filled epoxy resins, thereby permitting higher filler loading, to enhance the tinctorial power of pigments, and to render casting resins water-extendible. The titanate-phosphite adducts are the reaction products of one mole of a compound having the formula $(RO)_4Ti$ and two moles of di-substituted hydrogen phosphite, $(R'O)_2P(O)H$, where R and R' are monovalent alkyl, alkenyl, aryl, aralkyl or alkaryl. Both R and R' may be alkoxy, aroxy, bromo or chloro-substituted derivatives of the aforesaid groups. R may have from 1 to 18 carbon atoms, preferably 3 to 12, except where the titanates are used for water-extension, where R is preferably 6 to 12. R' may be from 3 to 18, preferably from 6 to 14.

14 Claims, No Drawings

TITANATE PHOSPHITE ADDUCTS AND THEIR USE

This is a division of application Ser. No. 653,772, filed Jan. 30, 1976, and now U.S. Pat. No. 4,080,353.

This invention relates to adducts of tetra-substituted titanates and di-substituted hydrogen phosphites; the use of such adducts for treating particulate fillers, including pigments; the compositions of fillers and the aforesaid adducts with epoxy resins and other casting resins; the reaction product of said adducts with aromatic polyamines; and the use of said reaction products for curing epoxide urethane resins; and compositions of certain of the adducts and casting resins. The titanate-phosphite adducts serve to reduce the viscosity of filled casting resins, thereby permitting higher filler loading, to enhance the tinctorial power of pigments, and to render casting resins water-extendible.

More specifically, the instant invention relates to filled resin compositions having improved physical properties obtained by linking the filler to the epoxy resin chain.

It is known that certain organic titanate esters may be used to treat the surfaces of inorganic fillers to enhance their compatibility with polymeric material. Such applications are shown in U.S. Pat. Nos. 3,697,474 and 3,697,475 issued to the Freeport Sulphur Company. These filled polymeric materials are well known and find application in fibers, sheet material and shaped solid articles. The aforesaid patents specifically relate to organic derivatives of ortho-titanic acid containing at least two hydrolyzable groups.

In accordance with the instant invention, it has been found that treating inorganic fillers with organic titanate-phosphite adducts imparts even greater advantages than that obtained by following the teachings of the aforesaid patents. This effect is particularly outstanding when the casting resin is an epoxide.

The use of the compositions of the present invention improves the rheology properties of filled resins, permits higher loading, and achieves more efficient use of pigments and opacifiers.

The addition of titanate-phosphite adducts gives the casting resins improved mechanical properties far better than those obtained heretofore. Stress, tensile strength, flexibility, shear resistance, adhesion in surface coating applications, resistance to chemical attack, and the advantages of cross-linking and wetting are obtained because the reaction product of the filler and the organic titanate salt is chemically bound to the resin. In all instances, the filler becomes more tightly incorporated in the polymeric structure. This bond, whether covalent or Van der Waal, results in a structure which is more readily able to transfer energy and therefore a stronger material.

More specifically, the organo-titanate salts which are claimed herein are adducts of di-substituted hydrogen phosphites having the formula $(R'O)_2P(C)H$ and tetra-substituted titanates having the formula $(RO)_4Ti$. These adducts are obtained by reacting one mole of the titanate compound with two moles of the phosphite compound. The R and the R' are monovalent alkyl, aryl, alkenyl, aralkyl or alkaryl, or alkoxy, aroxy, chloro or bromo-substituted derivative thereof. The alkoxy group as used herein includes polyoxyalkylene substitutions. The R and R' groups may be linear or branched, and may have from 1 to 4 substitutions. Broadly, P may have from 1 to 18 carbon atoms and R' from 3 to 18. Preferably, R' has from 6 to 14 carbon atoms. The preferred number of carbon atoms in the R depends on the particular application. Where the adduct is added for water extension, from 6 to 14 carbon atoms are preferred; however, in other filled systems, R may preferably be lless than 6. The optimum for a given system may be readily determined by those skilled in the art. In a particular molecule, all of the R groups may be the same or different, so long as they fall within the above class.

Examples of the phosphito-titanate adducts are:
tetramethoxypropyl di(dioctylphosphito)titanate;
tetraphenyl di(dibutylphosphito) titanate;
dimethyl, diphenyl di(diisopropylphosphito)titanate;
tetramethoxyphenyl di(dibutylphosphito) titanate;
tetramethyl di(diphenylphosphito)titanate;
tetra(chloroethyl) di(octyldecylphosphito)titanate;
tetra(chlorophenyl) di(dilaurylphosphito)titanate;
tetra(bromomethyl) di(dimethoxybutylphosphito)titanate;
tetraethyl di(dibenzylphosphito)titanate;
tetraisobutyl di(ditolylphosphito)titanate;
tetra t-butyl di(dixylylphosphito)titanate;
tetra-2-methoxyethoxyethyl di(di-2-chloro-ditridecylphosphito)titanate; and
methyl 2-hexyl 2-ethoxyethyl isooctyl di(2,4-dibromophenoxy n-hexylphosphito)titanate.

These materials may be readily prepared by reacting stoichiometric proportions of the titanate with the phosphite at temperatures and pressures necessary to maintain a liquid phase reaction. The preferred adducts are mobile liquids having a high flash point and a low pour point.

Examples of the R and R' groups are numerous. These include straight chain, branched chain and cyclic alkyl groups such as hexyl, heptyl, octyl, decyl, dodecyl, tetradecyl, pentadecyl, hexadecyl, octadecyl, nonadecyl, eicosyl, docosyl, tetracosyl, cyclohexyl, cycloheptyl and cyclooctyl; and alkenyl such as allyl.

Halo-substituted groups include bromohexyl, chlorooctadecyl, iodotetradecyl and chloroctadecyl. One or more halogen atoms may be present, as for example in dichlorohexyl or tetrabromooctyl. Examples of the alkoxyalkyl and alkoxyaryl type include methoxyhexyl, ethoxydecyl, methoxyphenyl, methoxynaphthyl and isopropoxyphenyl.

The aryl groups include the phenyl and naphthyl groups and substituted derivatives. Substituted alkyl derivatives include toluyl, xylyl, pseudocumyl, mesityl, isodurenyl, durenyl, pentamethylphenyl, ethylphenyl, n-propylphenyl, cumylphenyl, 1,3,5-triethylphenyl, diphenylmethyl and chlorophenylmethyl. Halo-substituted may be exemplified by chlorophenyl, dichlorophenyl, dibromotoluyl, and trichloroxylyl.

The amount of the titanate-phosphite adduct used is at least 0.01 part, preferably from 0.1 to 5 parts, and most preferably between 0.2 and 2 parts, per 100 of inorganic solid. The optimum proportions required are a function of the inorganic solid and the titanium salt selected, and the degree of the comminution, i.e., the effective surface area, of the inorganic solid. The reaction of the titanate takes place on the surface of the inorganic filler. The hydrolyzable group splits off and an organic hydrophobic surface layer is formed on the inorganic solid. The unmodified solid, in the absence of the titanates, is difficult to disperse in an organic medium because of its hydrophilic surface. The organo-titanium compound may be incorporated into an organic medium (low molecular weight liquids or higher molecular weight polymeric solids) with the inorganic solid. Alternatively, the organo titanate may be first reacted with the inorganic solid in the absence of an organic medium and thereafter admixed with the resin.

Also, according to the invention herein, the reaction with the RO groups on the organo-titanates may be carried out neat or in an organic medium to form a liquid, solid or paste-like solid dispersion which can be used in the compounding of the final polymeric system. Such dispersions are very stable, i.e., having little tendency to settle, separate, or harden on storage to a non-dispersible state.

By "casting resins" as used herein are meant liquid monomers or incompletely polymerized polymers, usually containing catalysts or curing agents, capable of becoming hard after they are cast in molds. By "coating resins" as used herein are meant liquid monomers or incompletely polymerized polymers, generally in a solvent or non-solvent extender, which are capable of application by brush, roller, spray or dipping. The casting and coating resins are thermosetting resins which are liquid under conditions of application. These include paints, varnishes, enamels and laquers. The materials of particular interest in the instant application are epoxy resins; polyester resins including alkyds, polyacrylates and polymethacrylates furans; and phenolics.

A wide variety of epoxy resins may be prepared in accordance with the subject invention. Reference may be made to U.S. Pat. No. 2,698,315, issued Dec. 28, 1954; U.S. Pat. No. 2,707,708, issued May 3, 1955; and U.S. Pat. No. 2,705,223, issued Mar. 29, 1955, all of which are incorporated herein by reference.

The epoxy resins are commonly complex polymeric reaction products of polyhydric alcohols with polyfunctional halohydrins such as epichlorohydrin and glyceryl dichlorohydrin. The products obtained may contain terminal epoxy groups, or terminal epoxy groups and terminal primary hydroxyl groups. See, for example, Column 6 of U.S. Pat. No. 2,872,428, issued Feb. 3, 1959.

Polyesters include materials prepared by reacting one or more glycols with one or more alpha, beta-ethylenically unsaturated polycarboxylic acid. Examples of such acids are maleic, fumaric, and itaconic and such glycols as ethylene, diethylene, triethylene, 1,3-propylene, 1,2-propylene, dipropylene, butylene or styrene glycol.

Alkyl resins are a type of unsaturated polyester modified with oil or a fatty acid. The polyacrylates and methacrylates are formed by the polymerization of methyl methacrylate and methyl acrylate, though the higher esters such as ethyl, butyl, lauryl and stearyl methacrylates and the ethylbutyl and 2-ethylhexyl acrylates are commonly used. Such resins are sometimes modified with non-acrylic monomers such as acrylonitrile, butadiene or styrene.

The furan resins are thermosetting resins obtained primarily by the condensation polymerization of furfural alcohol in the presence of a strong acid, sometimes in combination with formaldehyde or furfural aldehyde. The term also includes resins made by condensing phenol with furfuryl alcohol or furfural, and furfurylketone polymers.

Phenolic resins are a family of thermoset resins made by the reaction of phenols with aldehydes such as formaldehyde, acetaldehyde, or furfuryl aldehyde. For casting B-stage resins are generally used. Examples of the phenols are di- and trivalent phenols such as cresol, resorcinol and cardanol. In casting resin applications, a large excess of formaldehyde is generally used with sodium hydroxide as the catalyst. The reaction is usually carried out at about 64° C.

The filler may be particulate or fibrous and of varied shape or size, so long as the surfaces are reactive with the hydrolyzable group of the organo-titanium compound. Examples of inorganic reinforcing materials include metals, clay, carbon black, calcium carbonate, barium sulfate, silica, mica, glass and asbestos. Relative inorganic materials include the metal oxides of zinc, magnesium, lead, and calcium and aluminum, and iron filings and turnings. Examples of inorganic pigments include titanium dioxide, iron oxides, zinc chromate, and ultramarine blue. Examples of organic pigments include phthalocyanine blue, quinacyridone yellow, iron blue and naphthol blue. As a practical matter, the particle size of the particulate materials should not be greater than 1 mm, preferably from 0.1 micron to 500 micron.

The amount of filler used depends on the particular polymeric material, the filler and the property requirements of the finished products. Broadly, from 50 to 1500 parts of filler may be used based on 100 parts of polymer, preferably from 300 to 1000. The optimum amount may be readily determined by one skilled in the art.

It is imperative that the adducts be properly admixed with the filler to permit the surface of the latter to react sufficiently. The optimum amount of the titanium salt to be used is dependent on the effect to be achieved, the available surface area of and the bonded water in the filler.

Reaction is facilitated by admixing under the proper conditions. Optimum results depending on the properties of the titanium salt, namely, whether it is a liquid or solid, and its decomposition and flash points. The particle size, the geometry of the particles, the specific gravity, the chemical composition, among other things, must be considered. Additionally, the treated filler must be thoroughly admixed with the liquid resin. The appropriate mixing conditions depend on the type of polymer, its chemical structure, etc., as will be readily understood by those skilled in the art.

Where the filler is pretreated with the organic titanate, it may be admixed in any convenient type of intensive mixer, such as a Henschel or Hobart mixer or a Waring blender. Even hand mixing may be employed. The optimum time and temperature are determined to obtain substantial reaction between the inorganic material and the organic titanate. Mixing is performed under conditions at which the organic titanate is in the liquid phase, at temperatures below the decomposition temperature. While it is desirable that the bulk of the hydrolyzable groups be reacted in this step, this is not essential, since the substantial completion of the reaction may take place when the filler is admixed with the polymer.

Polymer processing, e.g., high shear mixing, is generally performed at a temperature well above the second order transition temperature of the polymer, desirably at a temperature where the polymers will have a low melt viscosity.

Temperatures for mixing the liquid resins with the treated filler are well known in the art and are typically performed at near ambient temperatures. A variety of mixing equipment, typically turbine, propeller or cement mixers, may be used.

When the organic titanate and the filler are dry-blended, thorough mixing and/or reaction is not always complete and the reaction may be substantially completed when the treated filler is admixed with the polymer. In this latter step, the organic titanate may also react with the polymeric material if one or more of the R' groups is reactive with the polymer.

In another embodiment of the invention, resins useful for coating or casting are made water-extendible. By adding the titanate adducts to the casting resins, it has been found possible to incorporate up to 50% water into the resin with only a minor amount of deterioration of the mechanical properties of the resultant casting or film. This discovery is of enormous economic significance, since it reduces the volume of volatile solvents needed to extend the resins to a usable level. Prior attempts to water-extend resins could not be achieved except by first reacting the conventional resins with hydrophilic materials, such as trialkanol amines. Unfortunately, this latter technique presented serious handling problems and caused a substantial loss of the mechanical properties in the resulting film.

Only certain of the phosphite-titanate adducts of the invention are suitable for this application. Referring to the above formula, it is necessary that R is at least 6, preferably at least 8, and most desirably from 10 to 12. Preferred species are tetraoctyl(dilaurylphosphito)titanate and tetradecyl(dioctylphosphito)titanate.

The casting resins may be made extendible by adding from 0.1 to 5 weight percent, preferably from 0.5 to 3 weight percent, of the phosphite-titanate adduct of the invention, based upon the weight of the resin. Based on 100 parts of resin by weight, from 10 to 100 parts of water may be added. It will be understood that the amount of water affects the strength and thickness of the resulting film as well as the viscosity of the resin.

In still another embodiment of the invention, the phosphite-titanate adducts serve to advance technology of curing epoxy resins and urethanes. By reacting the adducts with aromatic amine curatives, preferably diamines, tetramines and phenolic amines, the curing ability is significantly enhanced. This permits the curing of the epoxy or the urethane compound at considerably lower temperatures, as for example reducing the curing temperature from the conventional 120° C. to about room temperature. Naturally, such low temperature curing has substantial advantages, e.g., energy- and equipment-saving and less volatilization resulting in reducing odors and contamination. Furthermore, the use of these reaction products substantially increases the loading ability of the epoxy system because of a synergistic effect on the viscosity. With the practice of the invention, one can form epoxy resins of high chemical resistance without the need fo complex baking procedures.

The aromatic amines which may be reacted with the phosphite-titanate adducts of the invention are the primary, secondary or tertiary amines known to be curatives for epoxy and urethane resins. The commercially important compounds are m-phenylenediamine, 4,4'-methylenedianiline and blends thereof and diaminodiphenylsulfone. Phenolic amines include the tertiary amines, dimethylaminomethylphenol and tri(dimethylaminomethyl)phenol.

To form the curative reaction product of the invention, one mole of the aromatic amine is admixed with one mole of the phosphite-titanate adduct. The reaction may be carried out at temperatures from about 0° C. to about 250° C. Since the reaction is a surface reaction, as little as 0.1 to 1 mole of the adduct may be admixed with the amine.

The epoxy resins which may be cured in accordance with this embodiment of the invention are defined above. The polyurethanes are a family of resins produced by reacting diisocyanates with organic compounds containing two or more active atoms to form polymers having free isocyanate groups. A detailed description of these resins is given in U.S. Pat. No. 3,060,137, issued Oct. 23, 1962. These groups, under the influence of heat or catalyst, will react with each other or with water, glycols, etc., to form thermosetting materials. The casting resins are viscous liquids or low melting solids which are generally marketed as prepolymers. Polyurethanes are also widely used to form foams, as is well known in the art.

PREPARATION OF TETRAALKOXY TITANIUM DI(DIESTER)PHOSPHITES

These compounds may in general be prepared by mixing diester phosphites with tetraalkyl titanates in a 2:1 mole ratio at temperatures of from about −20° to about 150° C. Mixing temperatures are preferably selected so that both materials are liquids. The vapor pressure at the reaction conditions must be kept low or adequate precautions taken to handle the material under elevated pressure. If the reactants are mixed in other than stoichiometric 2:1 ratio, the 2:1 product will nonetheless form except that it will be in admixture with the excess reactant. Such mixtures are less effective than the pure titanate di(diester)phosphites for many applications, e.g., alkyds, polyesters. An excess of tetraalkyl titanate leads to hydrolytic instability and an excess of diester phosphite leads to prolonged resin hardening times and thermal degradation.

There is ordinarily little thermal evidence of reaction between most diester phosphites and tetraalkoxy titanates and frequently little visual indication of reaction is observable. However, a yellow color results on admixture of tetraisopropyl titanate and di(2-ethylhexyl)phosphorus acid, both reactants of which are colorless. Similarly, admixture of colorless tetraoctyl titanate with di-cresylphosphorus acid produces an orange-red product. There is no volatile by-product formation as measured by gas chromatography (less than 100 ppm) on mixing. By reacting the appropriate di(ester)phosphite with the appropriate tetraalkyl titanate in a molar ratio of 2:1 at room temperature, the following compounds of the invention were prepared. The melting point and specific gravity for each product are shown in the table below:

Table I

| Physical Properties of Selected Adducts | | |
|---|---|---|
| | M.P. ° C. | Sp.G. at 25° C. |
| Tetraisopropyl titanate di(dioctyl)phosphite | <−20 | 0.964 |
| Tetra-2-butoxyethyl titanate di(di-3-chloropropyl)phosphite | <−20 | 0.981 |
| Tetraoctyl titanate di(dilauryl)phosphite | <−20 | 0.953 |
| Tetraoctyl titanate di(dicresyl)phosphite | ∼ 0 | 0.969 |

Example 1

This example shows the effect on viscosity of the organo-titanates on a sand-filled epoxy resin (Epon 828, a trademark of Shell Chemical Company for an epoxy resin which is a condensation product of epichlorohydrin and bis-phenol A having a molecular weight of approximately 13,000). To 100 parts of this resin and 12 parts of diethylene triamine were added incremental amounts of sand (Colorquartz No. 28 filler, a trademark of 3M Company) until, after 2 minutes of mixing, the viscosity equalled 200,000 centipoise. Following the same procedure, three solutions were prepared in accordance with the practice of the invention. To the first solution was added tetraisopropyl di(dioctyl)phosphito titanate, to the second tetraisopropyl di(dilauryl)phosphito titanate, and to the third tetraoctyl di(dilauryl)phosphito titanate. Incremental amounts of filler were again added until, after 2 minutes of mixing, the viscosity was 200,000 centipoise. The amount of titanate added was approximately 1% based on the total filler added.

Table II below shows the filler loading to achieve the aforesaid viscosity:

Table II

| Titanate | Parts Sand per Part of Solution |
|---|---|
| None - Control | 3.5 |
| Tetraisopropyl di(dioctyl)-phosphito titanate | 6.1 |
| Tetraisopropyl di(dilauryl)-phosphito titanate | 7.2 |
| Tetraoctyl di(dilauryl)-phosphito titanate | 10.7 |

The above example shows that the compounds of the invention permit the use of considerably more filler as compared to the standard case where no titanate is added. This volumetric extension of the composition is a particular advantage since the filler materials are substantially less costly than the epoxy resin.

Example 2

The use of the organo-titanates of the invention in an epoxy paint system is shown in this example. Two polyamide cured epoxy compositions are prepared, one using the tetraisopropyl di(dioctyl)phosphito titanate of the invention. The formulations are shown in the attached Table.

Table III

| Base A | Non-Titanate | Titanate |
|---|---|---|
| Epoxy Resin* | 607 | 607 |
| Solvent | 285 | 285 |
| Lecithin | 8 | 8 |
| Pine Oil | 8 | 8 |
| Flow Control Agent | 4 | 4 |
| TiO2 | 300 | 300 |
| Mg Silicate | 170 | 670 |
| Clay | 150 | 650 |
| BaSO4 | 150 | 150 |
| Fumed Silica** | 20 | 20 |
| Tetraisopropyl di(dioctyl)phosphato titanate | — | 18 |

*Resypox 1628 (trademark of Resyn Corporation)
**Cab-O-Sil (trademark of Cabot Corporation)

It will be noted that in the composition containing the titanate, though its filler loading was more than double the prior art formulation, the TiO2 content could be held constant, since the two formulations had substantially the same viscosity.

The paints were then applied as a 3 mil thickness wet coating to a ceramic test panel. A comparison of the painted surfaces showed that the titanate-containing sample had increased hiding and whitening power, increased flexibility, less chalking and greater chemical resistance than the control. This latter property was illustrated by treatment with concentrated HCl, nitric and phosphoric acids applied to the dried paint. In each case, the titanate-treated film resisted attack while the untreated film deteriorated and dissolved.

Thermal stability was also tested using a 3 mil wet drawdown. The tests were performed at 250° F. for a period of 8 hours. While non-treated film thermally degraded, the titanate-treated film was left unchanged.

Example 3

This example shows the effect of tetrahexyl, di(dilauryl)phosphito titanate on the epoxy-curative characteristics of methylene dianiline and of paraphenylene diamine.

Suspensions of 500 parts by weight of aluminum hydrate having a nominal particle size of 100 to 150 microns in a solution comprised of 30 parts of amine and 70 parts of Epon 828 (unmodified epoxy resin) were prepared with and without titanate as shown below. The time required to effect a hard cure was determined by maintaining the samples at 23°±4° C. over the test period.

Table IV

| Component part by wt. | Suspension | | | |
|---|---|---|---|---|
| | A | B | C | D |
| Epoxy resin | 70 | 70 | 70 | 70 |
| Methylene dianiline | 30 | 30 | — | — |
| p-Phenylene diamine | — | — | 30 | 30 |
| Aluminum trihydrate | 500 | 500 | 500 | 500 |
| Tetrahexyl di(dilauryl)-phosphito titanate | — | 15 | — | 15 |
| Cure time, hours | >120 | ca.11 | >120 | ca.6 |

The above shows the utility of the indicated titanate as an epoxy resin cure enhancer for aromatic amine-cured system.

Example 4

This example shows that, by using the titanate-phosphite adducts of the invention, conventional solvent-based alkyl resins can be extended with water.

A solvent-based alkyd, Pratt & Lambert Vitralite long life dull-neutral enamel No. 2297, was tested. This paint contains 43.3% $CaCO_3$, 2.4% silicate, 19.0% soya linseed alkyd resin, 0.7% dryer and 34.6% petroleum distillate. Water separation occurred upon the addition of 5% water. Two percent of tetraoctyl(dilauryl)phosphito titanate based on the total paint (approximately 4% based on solids) was added to a sample of the paint. Thereafter, water was added up to 50% by weight. No water separation was observable. The film integrity of a 3 mil drawdown was maintained over the dilution range though the hiding power decreased.

The aforesaid example is of extreme significance since it shows substantial extension of an alkyd resin film with perhaps one of the most readily available commodities available, namely, water. To be able to extend alkyd resins to this degree is wholly unexpected.

Example 5

This example shows the use of tetraisopropyl, di(dilauryl)phosphito titanate for improving the physical properties of epoxy flooring compounds.

Because the organo-titanates of the invention decrease the viscosity of the filled epoxy compositions, it is necessary to increase the filler loading in order to provide adequate viscosity for certain applications, as for example in the practical application of flooring compounds and grout. Fortunately, because the filler is stronger than the resin, this increase in filler loading contributes to the strength of the flooring compound.

Table V shows a conventional flooring compound and two compounds containing the aforesaid organo-titanate. Additionally, data is provided showing the results of tests on the flooring formulation before and after curing:

Table V

|  | 1 | 2 | 3 |
|---|---|---|---|
| Epon 828 | 100 | 100 | 100 |
| Tetraisopropyl, di(dilauryl)-phosphito titanate | — | 6.66 | 8.88 |
| Tetraethylene triamine | 13 | 13 | 13 |
| #1 Sand | 444 | 666 | 888 |
| Slump Test | 2" | 11¼" | 2" |
| Trowel "Feel" | Good | Soupy | Good |
| Compression Strength, psi | 58,000 | 46,000 | 75,000 |

The above results show that the addition of titanate in Example 2 decreased the viscosity of the formulation to such an extent that the trowel "feel" was too soupy for practical application. This fact is also shown in the slump test. On the other hand, formulation 3 shows that even higher filler loadings, twice that obtainable with the conventional formulation, restored the viscosity so that a satisfactory trowel feel was obtained. Additionally, the compression strength of the hardened composition was substantially increased.

Example 6

This example shows the increase in filler loading which may be obtained by adding tetraoctyl di(-dilauryl)phosphito titanate to an epoxy floor topping compound. The conventional compositions of the prior art contain 80% inorganic aggregate, using as the aggregate a grey-ground silica mortar manufactured by Perma Flex Products Co., Inc. The addition of 1% titanate based on filler brought the loading to 88% total organics, an increase of 56% over the conventional composition. The following table shows the two compositions compared.

Table VI

|  | 1 | 2 |
|---|---|---|
| Epon 828 | 100 | 100 |
| Hardener* | 20 | 20 |
| Tetraoctyl di(dilauryl)-phosphito titanate | — | 8.5 |
| Mortar Aggregate | 500 | 850 |
|  | 620 | 970.5 |

*Celanese Corp. Epicure 874 formulation containing triethylenetetramine, nonylphenol, diethylenetriamine and fatty acid.

In preparing the formulation, the titanate was added to the epoxy resin and hardener was stirred in. The aggregate was then poured into the liquid mix. Both formulations had comparable trowel "feel" and the titanate treated compound appeared stronger.

Example 7

This example shows the effect of the ratio of the reactants used in forming the titanate phosphite adducts as applied to an epoxy formulation. The formulation used contained 87 parts Epon 828, 13 parts of diethylenetriamine, 1% of the titanate-phosphite adduct (based on sand) and sufficient Berley #1 sand to achieve a viscosity of 400,000 centipoise ten minutes after mixing in a high intensity mixer. The components were added in the order stated. The sand was added incrementally until the aforesaid viscosity was achieved. The following table shows the tensile strength of a sample hand-packed and cast in a polypropylene mold, evaluated after 48 hour cure times.

The following table shows the results obtained. In all cases, the titanate used was tetraoctyl titanate:

Table VII

| Mole Ratio Titanate: Phosphite | Phosphite Reactant | Parts Sand per 100 Parts Resin | 48 Hour Tensile Strength |
|---|---|---|---|
| 1:2 | Di(dilauryl)phosphite | 600 | 320 psi |
| 1:1 | Di(dilauryl)phosphite | 450 | 280 psi |
| 1:4 | Di(dilauryl)phosphite | 350 | 300 psi |
| 1:2 | Tri(lauryl)phosphite | 250 | 250 psi |
| — | None | 275 | 220 psi |

The above table clearly shows that the reaction product of 1 mole of titanate and 2 moles of phosphite give the best loading and tensile strength characteristics. Furthermore, it is clear that a triester phosphite is not equivalent to the diester, since no change in loading and tensile strength is achieved.

Example 8

Flooring compounds were prepared using 88 parts of Epon 828, 12 parts of triethylene-tetramine and with the amounts of tetraalkoxy titanium di(diester)phosphite and sand (Berkley #1) shown below. The formulations were cured at room temperature and the strength measured after five days. Table VIII shows the results obtained:

Table VIII

| Additive | Parts by Weight | Sand, Parts | Compressive Strength, psi | Tensile Strength, psi |
|---|---|---|---|---|
| None | — | 200 | 12 M | 0.9 M |
| " | — | 250 | 10.9 M | 0.76 M |
| " | — | 300 | 9.7 M | 0.71 M |
| " | — | 350 | NP | NP |
| Tetraisopropoxy titanium di(dioctyl)phosphite | 2 | 200 | 11.8 M | 1.1 M |
| " | 2.5 | 250 | 11.4 M | 0.92 M |
| " | 3.0 | 300 | 9.9 M | 0.88 M |
| " | 4.0 | 400 | 8.9 M | 0.86 M |
| " | 4.5 | 450 | NP | NP |
| Tetraoctyloxy titanium di(dilauryl)phosphite | 2 | 200 | 13.2 M | 1.2 M |
| " | 2.5 | 250 | 11.8 M | 1.1 M |
| " | 3 | 300 | 11.2 M | 0.98 M |
| " | 4 | 400 | 9.9 M | 0.92 M |
| " | 5 | 500 | 8.7 M | 0.87 M |
| " | 5.5 | 550 | NP | NP |

NP — Not Pourable

The data show that not only is the loadibility increased but so is the mechanical strength of the titanate-phosphite adducts of the invention over a wide range of sand loadings.

Example 9

This example shows the use of tetraalkyl titanium di(diester)phosphite adducts on the dispersion of 60% magnesium oxide in a hydrocarbon vehicle. The vehicle composition was about 85% paraffin oil, 4% paraffin wax, 10% polybutene. The amount of titanate was 1.2%, or 2% by weight based on the magnesium concentration.

The following table shows the penetrometer values for the various materials tested.

Table IX

| Titanate Added | Penetrometer at 25° C. |
|---|---|
| None | 30 |
| Tetraoctyl titanate | 85 |
| Tetraisopropyl titanate di(dioctyl)phosphite | 240 |
| Tetraoctyl titanate di(dilauryl)phosphite | 200 |

The above table shows that the titanates of the invention, namely, the last two shown in the table, substantially improve the penetrometer values. The tetraoctyl titanate, while having some effect, was substantially inferior to those of the invention. A higher penetrometer reading shows that a softer, more easily dispersed material is obtained.

Example 10

This example shows the use of the titanate-phosphite adducts of the invention in furan resin systems. The particular resin selected was a copolymer of furfural and furfuryl alcohol in a 1:1 weight ratio. The filler was a quartzite foundry sand containing 6% by weight of a methylene dianiline curative.

All the samples were prepared by admixing resin with the titanate compound and thereafter rapidly and intensively mixing in sand increments to a trowelable composite. The compositions contained 1% titanate based on the total sand added. The composites were cured at ambient temperature for 7 days and thereafter evaluated for compressive strength.

The following table shows the sand loading (parts of sand per part by weight of other components) of the trowelable compositions and the compressive strength of the cured composition.

Table X

| Titanate | Sand Load Ratio | Compressive Strength, psi |
|---|---|---|
| None | 7.5 | 5800 |
| Tetraisopropyl titanate di(dilauryl)phosphite | 7.5 | 4600 |
| " | 12.0 | 7300 |
| Tetra(triethyleneglycol monomethylether)titanate di(dicresyl)phosphite | 7.5 | 5100 |
| " | 14.6 | 7750 |

The above table shows that the compositions using the phosphite-titanate adducts of the invention improved compressive strength and loadability vs. the control. The highest compressive strength was achieved with higher loadings (the third and fifth formulations). Loadings above eight are not useful without the titanate-phosphite adducts because of insufficient fluidity.

Example 11

This example shows the application of the invention to improving the strength of phenolic resins filled with alundum. The following formulation was prepared: 25 parts phenolic resin (Bakelite BRNA-5345); 70 parts alundum (nominal averge size 35 micron); 5 parts hexamethylene tetramine; amount of titanate adduct as shown in Table XI below. The above mixture was cured for 30 minutes at 350° F. and the tensile strength measured. The following table shows the results obtained.

Table XI

| Titanate Adduct | Weight % on Alundum | Tensile Strength, psi |
|---|---|---|
| None | — | 400 |
| Tetraisopropyl di di(O-methoxyphenyl)phosphite | 1 | 650 |
| Tetraisopropyl di(dicumylphenyl)phosphite | 0.6 | 520 |
| Tetraisopropyl di(dicumylphenyl)phosphite | 1 | 540 |
| Dicumyl phosphorus acid | 1 | 380 |
| Tetraisopropyl titanate | 1 | 420 |

The above table shows the marked improvement on the tensile strength of the phenolic resin. This should be compared with the absence of improvement when the individual reactants are added separately.

Example 12

This example demonstrates the effect of the titanate-phosphite adducts of the invention on the flexural strength of polyester compositions. The following formulation was prepared: 100 parts Paraplex P-43 (trademark of Rohm & Haas); 100 parts aluminum hydrate (100 to 200 mesh); 0.5 part catalyst (methyl ethyl ketone peroxide); 1 part titanate. The following table shows the flexural strength of the cured composition and the pot life of the formulation. Pot life is defined as the time after which the formulation no longer undergoes plastic flow under stress.

Table XII

| Titanate | Flexural Strength, psi | Pot Life, Hours |
|---|---|---|
| None | 10,500 | 0.5 |
| Tetraisopropyl di(dialkyl)phosphite | 18,000 | 2 |
| Tetraoctyl di(dioctyl)phosphite | 14,000 | 3.5 |
| tetraoctyl tetra(dioctyl)phosphite | (no cure) | >24 |

The above table shows that the addition of the phosphite adduct improves the flexural strength in each and every case by a significant amount. Additionally, the pot life is lengthened substantially. The advantage of this is that larger batches may be prepared and the time for reworking of preliminary applications is increased. The last formulation, which is not within the scope of the invention, is clearly not useful.

Example 13

This example shows that liquid epoxy resin compositions containing the adducts of the invention can be cured with anhydride curatives in addition to the amine cures of the prior examples. The controlled composition contains a Ciba-Geigy Corp. modified liquid epoxy resin 6005 type, 100 grams; octyl succinic anhydride, 25 grams; and aluminum silicate (325 mesh), 200 grams. The formulation of the invention was the same except 300 grams of filler were used and 3 grams of tetraisopropyl, di(dilauryl)phosphito titanate added. The formulations were both cured at 205° C. for one hour.

Using a standard ASTM flexural test, it was determined that the control was 15,000 psi, while the compound of the invention, despite higher loading, had a flexural strength of 20,000 psi, a 33% improvement.

Example 14

Adducts of alkenyloxytitanates and di(diester)-phosphites may be used in radiation-cured unsaturated polyesters to effect cure densifications. These adducts include octyl triallyl titanate di(dilauryl)phosphites and isopropyl trimethallyl titanate di(dilauryl)phosphites. This provides improved physical properties for the resulting composition.

We claim:

1. A curing composition comprising an admixture of one mole of an aromatic amine with an adduct of a tetra-substituted titanate and a di-substituted hydrogen phosphite.

2. The curing composition of claim 1 wherein the adduct is of one mole of a tetra-substituted titanate having the formula $(RO)_4Ti$ and two moles of a di-substituted hydrogen phosphite having the formula $(R'O)_2P(O)H$ wherein R and R' are monovalent alkyl, alkenyl, aryl, aralkyl, alkaryl, alkoxy or aryloxy groups and wherein R has from 1 to 18 carbon atoms and R' from 3 to 18 carbon atoms.

3. A polymeric composition which comprises an admixture of an epoxy resin or a urethane resin with a curing system comprising an admixture of (A) an aromatic amine curing agent and (B) an adduct of one mole of a tetra-substituted titanate and two moles of a di-substituted hydrogen phosphite.

4. A polymeric composition of claim 3 wherein the tetra-substituted titanate has the formula $(RO)_4Ti$ and the di-substituted hydrogen phosphite has the formula $(R'O)_2P(O)H$ wherein R and R' are monovalent alkyl, alkenyl, aryl, aralkyl, alkaryl, alkoxy or aryloxy groups and wherein R has from 1 to 18 carbon atoms and R' from 3 to 18 carbon atoms.

5. A method of curing an epoxy of a polyurethane resin which comprises the improvement of carrying out the polymerization in the presence of a curing system comprising (A) an aromatic amine curing agent and (B) an adduct of one mole of a tetra-substituted titanate and two moles of a di-substituted hydrogen phosphite.

6. The method of claim 5 wherein the tetrasubstituted titanate has the formula $(RO)_4Ti$ and the disubstituted hydrogen phosphite has the formula $(R'O)_2P(O)H$ wherein R and R' are monovalent alkyl, alkenyl, aryl, aralkyl, alkaryl, alkoxy or aryloxy groups and wherein R has from 1 to 18 carbon atoms and R' from 3 to 18 carbon atoms.

7. A water-extended resin composition with comprises a resin for coating or casting, an organic titanate compound which is an adduct of one mole of a tetrasubstituted titanate and two moles of a dialkyl hydrogen phosphite, and from 10 to 100%, based on the weight of resin, of water.

8. The composition of claim 7 wherein a filler is also present.

9. A method of water-extending a resin composition useful for coating or casting which comprises adding to such resin from 0.1 to 5 weight percent based on resin of an organic titanate compound which is an adduct of one mole of a tetra-substituted titanate and two moles of a dialkyl hydrogen phosphite.

10. The method of claim 9 wherein the organic titanate compound is an adduct of one mole of a tetra-substituted titanate having the formula $(RO)_4Ti$ and two moles of a di-substituted hydrogen phosphite having the formula $(R'O)_2P(O)H$ wherein R and R' are monovalent alkyl, alkenyl, aryl, aralkyl, alkaryl, alkoxy or aryloxy groups and wherein R has from 6 to 14 carbon atoms and R' from 3 to 18 carbon atoms.

11. A resin composition which comprises a coating or casting resin containing an organo-titanate compound which is an adduct of one mole of a tetra-substituted titanate having the formula $(RO)_4Ti$ and two moles of a di-substituted hydrogen phosphite having the formula $(R'O)_2P(O)H$ wherein R and R' are monovalent alkyl, alkenyl, aryl, aralkyl, alkaryl, alkoxy or aryloxy groups and wherein R has from 1 to 18 carbon atoms and R' from 3 to 18 carbon atoms.

12. The resin composition of claim 11 wherein the resin is an epoxy resin, a polyester resin, a furan resin or a phenolic resin.

13. The composition of claim 11 wherein the resin composition is water-extendible and R has from 6 to 14 carbon atoms.

14. The water-extended resin composition of claim 7 wherein the organic titanate compound is an adduct of one mole of a tetra-substituted titanate having the formula $(RO)_4Ti$ and two moles of a di-substituted hydrogen phosphite having the formula $(R'O)_2P(O)H$ wherein R and R' are monovalent alkyl, alkenyl, aryl, aralkyl, alkaryl, alkoxy or aryloxy groups and wherein R has from 6 to 14 carbon atoms and R' from 3 to 18 carbon atoms.

* * * * *